United States Patent
Nelson

(10) Patent No.: US 7,197,355 B2
(45) Date of Patent: *Mar. 27, 2007

(54) VARIABLE-MOTION OPTICAL TOMOGRAPHY OF SMALL OBJECTS

(75) Inventor: Alan C. Nelson, Gig Harbor, WA (US)

(73) Assignee: VisionGate, Inc., Gig Harbor, WA (US)

( * ) Notice: Subject to any disclaimer, the term of this patent is extended or adjusted under 35 U.S.C. 154(b) by 572 days.

This patent is subject to a terminal disclaimer.

(21) Appl. No.: 10/126,026

(22) Filed: Apr. 19, 2002

(65) Prior Publication Data

US 2003/0199758 A1   Oct. 23, 2003

(51) Int. Cl.
*A61B 5/05* (2006.01)

(52) U.S. Cl. ............ 600/425; 382/131; 382/132; 600/473; 600/476; 356/432

(58) Field of Classification Search ........ 600/473–476, 600/425, 427; 382/128, 133, 131; 356/432; 378/4, 8, 11, 21, 23, 25
See application file for complete search history.

(56) References Cited

U.S. PATENT DOCUMENTS

| | | |
|---|---|---|
| 3,470,373 A | 9/1969 | Brewer |
| 3,497,690 A | 2/1970 | Wheeless, Jr. |
| 3,598,471 A | 8/1971 | Baldwin |
| 3,657,537 A | 4/1972 | Wheeless, Jr. |
| 3,748,468 A | 7/1973 | Hartman |
| 3,833,762 A | 9/1974 | Gudmundsen |
| 3,960,449 A | 6/1976 | Carlton |
| 3,999,047 A | 12/1976 | Green |
| 4,175,860 A | 11/1979 | Bacus |
| 4,183,623 A | 1/1980 | Haines |
| 4,200,353 A | 4/1980 | Hoffman |

(Continued)

FOREIGN PATENT DOCUMENTS

WO    WO 02/095476 A2    11/2002

OTHER PUBLICATIONS

Schmitz, "Perfomance Characteristics of a Silicon Photodiode (SiPD) Based Instrucment for Fast Functional Optical Tomography," undated, SUNY Downstate Medicial Center Brooklyn, NY.

(Continued)

*Primary Examiner*—Eleni Mantis Mercader
(74) *Attorney, Agent, or Firm*—George A. Leone

(57) ABSTRACT

Motion of an object of interest, such as a cell, has a variable velocity that can be varied on a cell-by-cell basis. Cell velocity is controlled in one example by packing cells into a capillary tube, or any other linear substrate that provides optically equivalent 360 degree viewing access, so that the cells are stationary within the capillary tube, but the capillary tube is translated and rotated mechanically through a variable motion optical tomography reconstruction cylinder. The capillary tube motion may advantageously be controlled in a start-and-stop fashion and translated and rotated at any velocity for any motion interval, under the control of a computer program. As such, there are several configurations of the optical tomography system that take advantage of this controlled motion capability. Additionally, the use of polarization filters and phase plates to reduce light scatter and diffraction background noise is described.

13 Claims, 5 Drawing Sheets

U.S. PATENT DOCUMENTS

| | | | |
|---|---|---|---|
| 4,293,221 | A | 10/1981 | Kay |
| 4,657,676 | A | 4/1987 | Keary |
| 4,858,128 | A | 8/1989 | Nowak |
| 4,891,829 | A | 1/1990 | Deckman |
| 4,966,576 | A | 10/1990 | Schulz |
| 5,141,609 | A | 8/1992 | Sweedler et al. |
| 5,308,990 | A | 5/1994 | Takahashi et al. |
| 5,312,535 | A | 5/1994 | Waska et al. |
| 5,321,501 | A | 6/1994 | Swanson et al. |
| 5,402,460 | A | 3/1995 | Johnson |
| 5,630,938 | A | 5/1997 | Feller |
| 5,668,887 | A | 9/1997 | Parker et al. |
| 5,676,631 | A | 10/1997 | Kunz |
| 5,680,484 | A | 10/1997 | Ohyama et al. |
| 5,710,429 | A | 1/1998 | Alfano et al. |
| 5,741,411 | A | 4/1998 | Yeung et al. |
| 5,760,901 | A | 6/1998 | Hill |
| 5,760,951 | A | 6/1998 | Dixon et al. |
| 5,828,408 | A | 10/1998 | Mottin et al. |
| 5,848,123 | A | 12/1998 | Strommer |
| 5,880,838 | A | 3/1999 | Marx et al. |
| 5,915,048 | A | 6/1999 | Hill et al. |
| 5,987,158 | A | 11/1999 | Meyer |
| 6,005,617 | A | 12/1999 | Shimamoto et al. |
| 6,026,174 | A | 2/2000 | Palcic |
| 6,038,067 | A | 3/2000 | George |
| 6,072,624 | A | 6/2000 | Dixon et al. |
| 6,091,983 | A | 7/2000 | Alfano et al. |
| 6,165,734 | A | 12/2000 | Garini |
| 6,201,628 | B1 | 3/2001 | Basiji |
| 6,211,955 | B1 | 4/2001 | Basiji |
| 6,215,587 | B1 | 4/2001 | Alfano et al. |
| 6,248,988 | B1 | 6/2001 | Krantz |
| 6,249,341 | B1 * | 6/2001 | Basiji et al. ................. 356/73 |
| 6,251,586 | B1 | 6/2001 | Mulshine |
| 6,251,615 | B1 | 6/2001 | Oberhardt |
| 6,252,979 | B1 | 6/2001 | Lee |
| 6,312,914 | B1 | 11/2001 | Kardos et al. |
| 6,330,106 | B1 * | 12/2001 | Greenwald et al. ......... 359/398 |
| 6,388,809 | B1 | 5/2002 | MacAulay |
| 6,452,179 | B1 | 9/2002 | Coates et al. |
| 6,529,614 | B1 | 3/2003 | Chao et al. |
| 6,591,003 | B2 * | 7/2003 | Chu et al. ................... 382/133 |
| 2001/0012069 | A1 | 8/2001 | Derndinger et al. |
| 2002/0045525 | A1 | 4/2002 | Marziali |
| 2002/0161534 | A1 | 10/2002 | Adler et al. |
| 2002/0173034 | A1 | 11/2002 | Barbera-Guillem |

OTHER PUBLICATIONS

Schmitz, "Instrumentation for Real-Time Dynamic Optical Tomography," undated, SUNY Downstate Medicial Center Brooklyn, NY.

Ong, SH, Development of an imaging flow cytometer. Anal Quant Cytol Histol 9(5)pp. 375-382, 1987.

Farichild Imaging, Preliminary Data Sheet CCD525, TDI, Time Delay and Integration Sensor, Jan. 12, 2001.

Farichild Imaging, Preliminary Data Sheet CCD582, TDI, Time Delay and Integration Sensor, Jan. 18, 2000.

Shapiro, HM, *Practical Flow Cytometry*, 3rd ed., Wiley-Liss, 1995.

HJ Tiziani and MI Uhde, Three-dimensional analysis by a microlens array confocal arrangements (*Applied Optics* 33, 567 [1994]).

Bayat, S, Le Duc, G, Porra, L, Berrruyer, G, Nemoz, C, Monfraix, S, Fiedler, S, Thomlinson, W, Suortti, P, Standertskjold-Nordenstam, CG, and Sovijarvi, ARA, "Quantitative Functional Lung Imaging with Synchrotron Radiation Using Inhaled Xenon as Contrast Agent", Physics in Medicine and Biology 46(3287-99) 2001.

Bentley, MD, Ortiz, MC, Ritman, EL, and Romero, JC, "The Use of Microcomputed Tomography to Study Microvasculature in Small Rodents", American Journal of Physiology (Regulatory Integrative Comp Physiol) 282(R1267-R1279) 2002.

Cheng, PC, Lin, TH, Wang, G, Shinozaki, DM, Kim, HG, and Newberry, SP, "Review on the Development of Cone-beam X-ray Microtomography", Proceedings of the X-ray Optics and Microanalysis 1992, Institute of Physics Ser. No. 130, Kenway, PB, et al. (eds.), Manchester, UK, Aug. 31-Sep. 4, 1992, pp. 559-566.

Defrise, M, Clack, R, and Townsend, DW, "Image Reconstruction from Truncated, Two-dimensional, Parallel Projections", Inverse Problems 11(287-313) 1995.

Defrise, M, Noo, F, and Kudo, H, "A Solution to the Long-object Problem in Helical Cone-beam Tomography", Physics in Medicine and Biology 45(623-43) 2000.

Endo, M, Tsunoo, T, Nakamori, N, and Yoshida, K, "Effect of Scattered Radiation on Image Noise in Cone Beam CT", Medical Physics 28(4) (469-74) 2001.

Jorgensen, SM, Demirkaya, O, and Ritman, EL, "Three Dimensional Imaging of Vasculature and Parenchyma in Intact Rodent Organs with X-ray Micro-CT", Am. J. Physiology 275(Heart Circ. Physiol. 44) pp. H1103-H1114, 1998.

Kinney, JH, Johnson, QC, Saroyan, RA, Nichols, MC, Bonse, U, Nusshardt, R, and Pahl, R, "Energy-modulated X-ray Microtomography", Rev. Sci. Instrum. 59(1)pp. 196-197, 1988.

Kinney, JH and Nichols, MC, "X-ray Tomographic Microscopy (XTM) Using Synchrotron Ratiation", Annu. Rev. Mater. Sci. 22pp. 121-152, 1992.

Taguchi, K and Aradate, H, "Algorithm for Image Reconstruction in Multi-slice Helical CT", Medical Physics 25(4) pp. 550-561, 1998.

Yu, DF, Fessler, JA, and Ficaro, EP, "Maximum-Likelihood Transmission Image Reconstruction for Overlapping Transmission Beams", IEEE Transactions on Medical Imaging 19(11)pp. 1094-1105, 2000.

Sharpe, J, Ahlgren, U et al., "Optical Projection Tomography as a Tool for 3D Microscopy and Gene Expression Studies," SCIENCE, vol. 296, pp. 541-545, Apr. 19, 2002.

Sharpe, J, review, "Optical Projection Tomography as a New Tool for Studying Embryo Anatomy," *J. Anat.* (2003), pp. 175-181.

RH Anderson, "Close-up imaging of documents and displays with lens arrays," *Applied Optics* 18, 477 (1979).

Kak, A.C. and Slaney, M., *Principles of Computerized Tomographic Imaging*, IEEE Press, New York, 1988.

E.G. Steward, *Fourier Optics: An Introduction*, 2nd ed. (Halsted Press, New York, 1987).

A. Klug and J.L. Finch, "Structure of viruses of the papilloma-polyoma type," J. Mol. Biol., vol. 37, p. 1 (1968).

A. Klug, "Image analysis and reconstruction in the electron microscopy of biological macromolecules," Chem. Scripta, vol. 14, p. 245 (1978).

T.C. Wedberg and J.J. Stamnes, "Recent results in optical diffraction microtomography," Meas. Sci. Technol., vol. 7, p. 414 (1996).

Y. Li, et al., "Comparison of analog and digital Fourier transforms in medical image analysis," J. Biomed. Optics, vol. 7, p. 255 (2002).

Y. Xu et al., "Three-dimensional diffuse optical tomography of bones and joints," J. Biomed. Optics, vol. 7, p. 88 (2002).

H. Banda-Gamboa et al., "Spectral-Analysis of Cervical Cells Using the Discrete Fourier-Transform," Anal. Cell. Path., vol. 5(2), pp. 85-102 (1993).

D.E. Burger, et al., "Extraction of Morphilogical Features from Biological Models and Cells by Fourier Analysis of Static Light Scatter Measurements," Cytometry, vol. 2, No. 5, pp. 327-336 (1982).

M. Rozycka, et al., "Optical Diffraction as a Tool for Semiautomatic, Quantitative Analysis of Tissue Specimens," Cytometry, vol. 2, No. 4, pp. 244-248 (1982).

Almeida and Fuji, Fourier transform differences and averaged simularities in diatoms, Applied Optics, vol. 18, No. 10, pp. 1663-1667, (1979).

Smolinska and Dawidowicz, "Extraction of common or different part from optical images," Institute of Physics, Warsaw Technical University, 222-223.

Miles, CP, Jaggard, DL, "The Use of Optical Fourier Transforms to Diagnose Pleomorphism, Size and Chromatin Clumping in Nuclear Models," Anal Quant Cytol Histol vol. 3, No. 2, pp. 149-156, 1981.

Dziedzic-Goclawska, et al., "Application of the Optical Fourier Transform for Analysis of the Spatial Distribution of Collagen Fibers in Normal and Osteopetrotic Bone Tissue," Histochemistry (1982) 74:123-137.

Ostrowski, et al., "Application of Optical Diffractometry in Studies of Cell Fine Structure," Histochemistry (1983) 78:435-449.

Mareel, MM, et al., "Numerical Evaluation of Changes in the Cytoplasmic Microtubule Complex of C3H Mouse Cells by Optical Diffractometry and of Changesin Cell Shape by Fourier Analysis," Cytometry 7:18-24 (1986).

Bem, W, et al., "Modification of Chromatin Pattern in the Course of Terminal Differentiation During Human Granulocytopiesis: Optical Diffractometry Study," Cellular and Molecular Biology 33(5), 563-571 (1987).

Rozycka, M, et al., "Analysis of chromatin pattern in blood lymphocytes of healthy donors and in lymphoid cells of patients with chronic lymphocytic leukaemia," J. Clin. Pathol. 1988:41:504-509.

George, JS et al., "Virtual Pinhole Confocal Microscope," Physics Division Progress Report, www.lanl.gov/p/pdfs/papp_pinhole.pdf, (1999-2000).

Pawley, JB, *Handbook of Biological Confocal Microscopy*, Plenum Press, NY, 479-490 (1995).

Gilbert, P, "Iterative Methods for the Three dimensional Reconstruction of an Object from Projections," Journal of Theoretical Biology 36:105-17, 1972.

Oppenheim, BE, More Accurate Algorithms for Iterative 3 dimensional Reconstruction, IEEE Transactions on Nuclear Science NS-21:72-7, 1974.

Singer, JR, Grunbaum, FA, Kohn, P, and Zubelli, JP, "Image Reconstruction of the Interior of Bodies that Diffuse Radiation," Science 248(4958):990-3, 1990.

Mueller, K and Yage, R, "Rapid 3-D Cone-beam Reconstruction with the Simultaneous Algebraic Reconstruction Technique (SART) Using 2-D Texture Mapping Hardware", IEEE Transactions on Medical imaging 19(12):1227-37, 2001.

Bellman, SH, Bender, R, Gordon, R, and Rowe, JE, "ART is Science being A Defense of Algebraic Reconstruction Techniques for Three dimensional Electron Microscopy," Journal of Theoretical Biology 32:205-16, 1971.

Manglos, SH, Jaszcak, RJ, and Floyd, CE, "Maximum Likelihood Reconstruction for Cone Beam SPECT: Development and Initial Tests," Physics in Medicine and Biology 34(12):1947-57,1989, #1382.

Manglos, SH, Gagne, GM, Krol A, Thomas, FD, and Narayanaswamy, R, "Transmission Maximum-likelihood Reconstruction with Ordered Subsets for Cone Beam CT", Physics in Medicine and Biology 40(7):1225-41, 1995, #4389.

Hampel, U and Freyer, R, "Fast Image Reconstruction for Optical Absorption Tomography in Media with Radially Symmetric Boundaries", Medical Physics 25 (1):92-101, 1998.

Jiang, H, Paulsen, KD, and Osterberg, UL, "Frequency-domain Near-infrared Photo Diffusion Imaging: Initial Evaluation in Multitarget Tissuelike Phantoms", Medical Physics 25(2):183-93, 1998.

Herman, G, *Image Reconstruction from Projections: The Fundamentals of Computerized Tomography*, Academic Press, New York, 1980.

Paulsen, KD and Jiang, H, "Spatially Varying Optical Property Reconstruction Using a Finite Element Diffusion Equation Approximation", Medical Physics 22(691-701) 1995.

* cited by examiner

VARIABLE-MOTION OPTICAL TOMOGRAPHY OF SMALL OBJECTS

FIELD OF THE INVENTION

The present invention relates to optical tomographic (OT) imaging systems in general, and, more particularly, variable-motion optical tomography (VOT) where the motion of a small object, such as a biological cell, for example, is controlled by a mechanical motion system whose motion is not necessarily constant and/or unidirectional, but may be variable and multi-directional.

BACKGROUND OF THE INVENTION

U.S. application Ser. No. 09/927,151 of Alan C. Nelson, filed Aug. 10, 2001, now U.S. Pat. No. 6,522,775 issued Feb. 18, 2003, entitled "APPARATUS AND METHOD FOR IMAGING SMALL OBJECTS IN A FLOW STREAM USING OPTICAL TOMOGRAPHY," (hereinafter called the FOT design) is incorporated herein by this reference. In the aforesaid Nelson patent application, cell motion is accomplished in a flow stream, wherein cells in suspension move with constant velocity along the single flow axis of a capillary tube. The FOT design does not address the more general case where cell velocity and/or direction of motion are variable.

SUMMARY OF THE INVENTION

In one embodiment, the present invention provides a method for variable-motion optical tomography (VOT), wherein motion of an object of interest, such as a cell, has a variable velocity relative to the light path that can be varied on a cell-by-cell basis. Cell velocity is controlled in one example by packing cells into a capillary tube, or any other linear substrate that provides optically equivalent 360 degree viewing access, so that the cells are stationary within the capillary tube, while the capillary tube is translated and rotated mechanically through an optical tomography reconstruction cylinder. The capillary tube motion may advantageously be controlled in a start-and-stop fashion and translated and rotated at any velocity for any motion interval, under the control of a computer program.

DETAILED DESCRIPTION OF THE PREFERRED EMBODIMENTS

The invention is described herein with respect to specific examples relating to biological cells, however, it will be understood that these examples are for the purpose of illustrating the principals of the invention, and that the invention is not so limited. In one example, constructing a three-dimensional distribution of point densities and emission intensities within a microscopic volume allows the measurement of density and fluorescence at any location within the microscopic volume and determines the location of structures, molecules or molecular probes of interest. By using tagged molecular probes, the quantity of probes that attach to specific structures in the microscopic object may be measured. For illustrative purposes, an object such as a biological cell may be labeled with at least one tagged molecular probe, and the measured amount and location of this probe may yield important information about the disease state of the cell, including, but not limited to, various cancers such as lung, colon, prostate, breast, cervical and ovarian cancers, or infectious agents.

Figure 1:
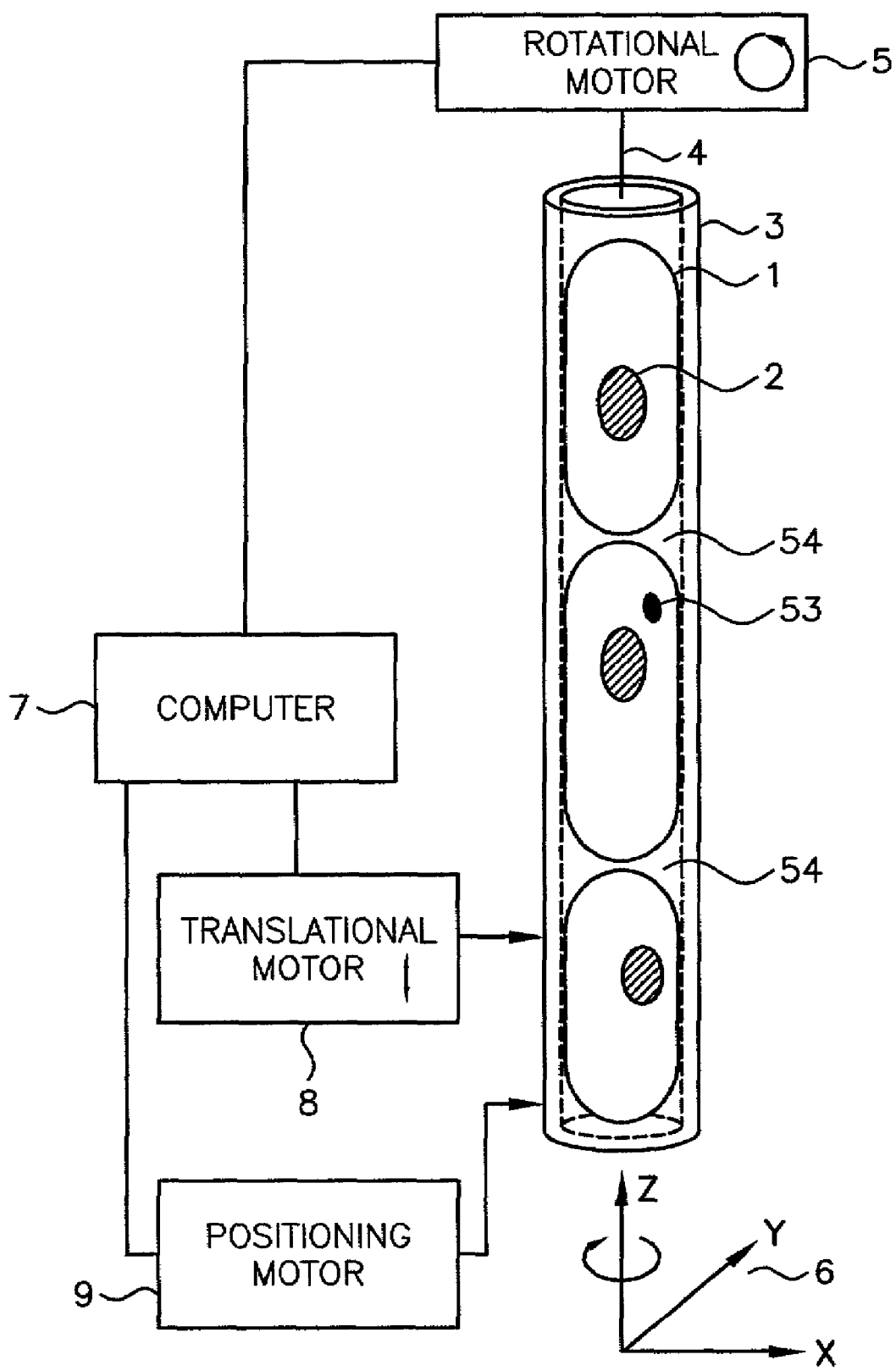
FIG. 1 schematically shows an example illustration of cells packed into a capillary tube as contemplated by an embodiment of the present invention.

Referring now to FIG. 1, there shown schematically is an example illustration of cells packed into a capillary tube as contemplated by an embodiment of the present invention. In this example embodiment, a section of the capillary tube 3 is filled with cells 1 that are packed rigidly into the tube. Each of the cells may include a nucleus 2. The capillary tube 3 has a central axis 4 oriented with reference to a coordinate system 6 having coordinates in the x, y and z-directions. In some instances, at least one molecular probe 53 may be bound within the cell. A computer 7 is coupled to provide control signals to a rotational motor 5 and a translational motor 8. It will be recognized that equivalent arrangements of one or more motors, gears or fluidics or other means of generating motion may also be employed to achieve the necessary translational and rotational motion of the capillary tube or other substrate. In some cases, one or more of the motors may be replaced by manual positioning devices or gears or by other means of generating motion such as hydraulics or piezoelectrics. The axis of translation is the z-axis, and rotation is around the z-axis. The positioning motor 9 is coupled to move the cell in a plane defined by the x,y-axes, substantially perpendicular to the central axis for the purpose of centration, as necessary.

It will be recognized that the curved surface of the capillary tube will act as a cylindrical lens and that this focusing effect may not be desirable in a projection system. Those skilled in the art will appreciate that the bending of photons by the tube can be eliminated if the spaces between the point source and the tube and between the tube and the detector surfaces are filled with a material 54 whose index of refraction matches that of the capillary tube and that the tube can be optically coupled (with oil or a gel, for example) to the space filling material.

Consider the present example of cells packed into a capillary tube. The cells may preferably be packed single file so that they do not overlap. The density of packing whole cells of about 100 microns in diameter into a capillary tube with diameter less than 100 microns can be roughly 100 cells per centimeter of tube length. For bare nuclei of about 20 microns in diameter, the packing can be roughly 500 nuclei per centimeter of tube length where the tube diameter is proportional to the object size, about 20 microns in this case. Thus, within several centimeters of capillary tube length, a few thousand non-overlapping bare nuclei can be packed. By translating the tube along its central axis 4, motion in the z-direction can be achieved. Moving the tube in the x,y-directions allows objects within the tube to be centered, as necessary, in the reconstruction cylinder of the optical tomography system. By rotating the tube around its central axis 4, a multiplicity of radial projection views can be produced. Moving the tube in the z-direction with constant velocity and no rotation simulates the special case of flow optical tomography.

One advantage of moving a tube filled with cells that are otherwise stationary inside the tube is that objects of interest can be stopped, then rotated, at speeds that permit nearly optimal exposure for optical tomography on a cell-by-cell basis. That is, the signal to noise ratio of the projection images can be improved to produce better images than may be usually produced at constant speeds and direction typical of flow systems. Objects that are not of interest can be moved out of the imaging system swiftly, so as to gain overall speed in analyzing cells of interest in a sample consisting of a multitude of cells. Additionally, the ability to stop on an object of interest, then rotate as needed for multiple projections, nearly eliminates motion artifacts. Still further, the motion system can be guided at submicron movements and can advantageously be applied in a manner that allows sampling of the cell at a resolution finer than that afforded by the pixel size of the detector. More particularly, the Nyquist sampling factor of 2 could be managed by the motion system moving in increments that fill half a pixel width, for example. Similarly, the motion system can compensate for the imperfect fill factor of the detector.

Figure 2:
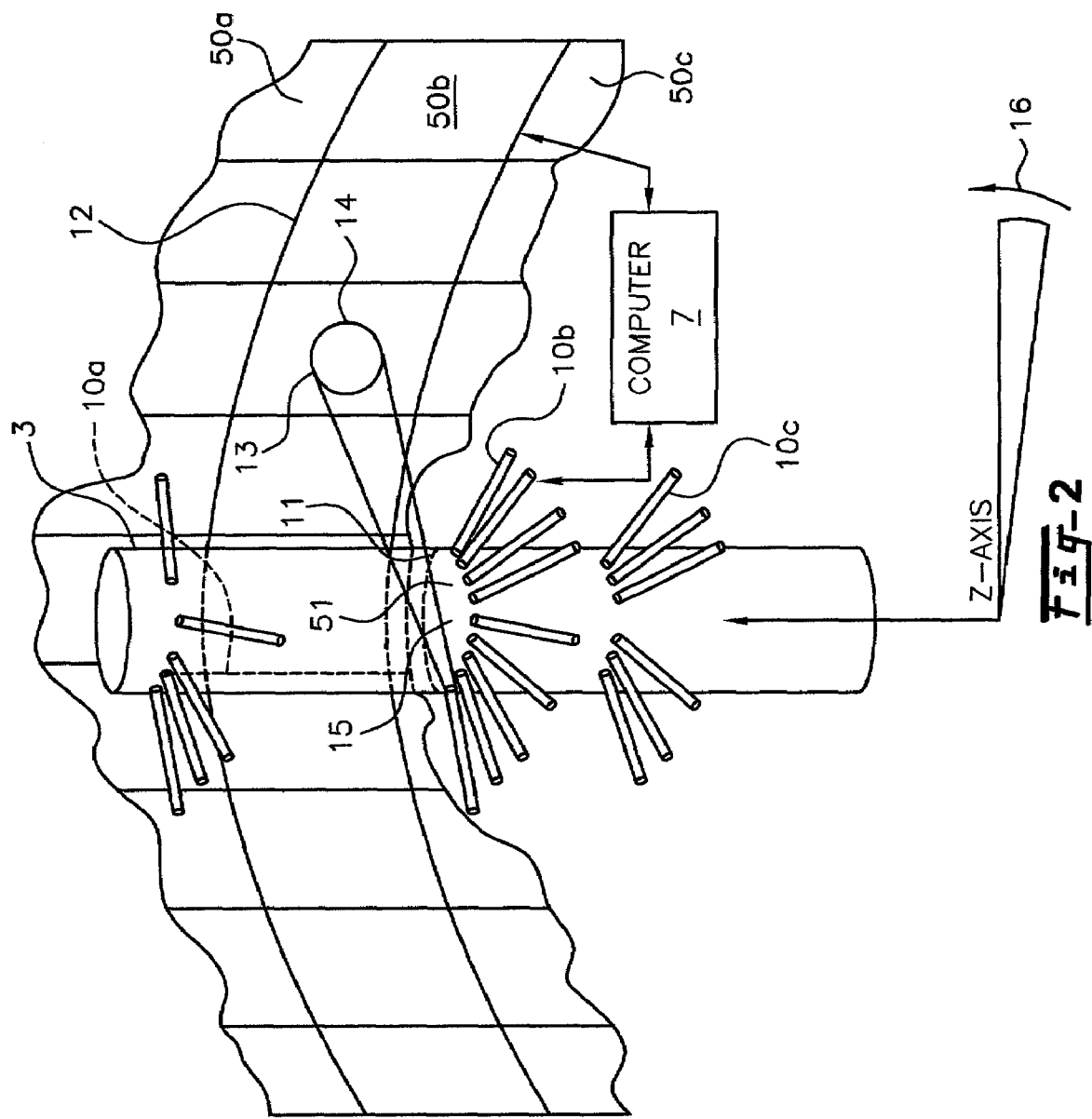
FIG. 2 schematically shows an example illustration of an optical tomography reconstruction cylinder as contemplated by an embodiment of the present invention.

Referring now to FIG. 2, there shown schematically is an example illustration of an optical tomography reconstruction cylinder as contemplated by an embodiment of the present invention. There shown is a VOT configuration with at least one point source 10b arranged at fixed angles along a circumference 11 at the tube wall. At least one detector 50b includes at least one detector surface 12, with surfaces opposing the at least one point source 10b, arranged on a wider circumference in the same plane as the point sources. Each point source projects a cone beam 13 onto a detector area 14 such that the projected cones do not overlap on the detector. It will be understood that other projection geometries may be acceptable such as those utilizing fan beam and pencil beam projections. To simplify the figure for understanding, only one cone beam has been shown, but it will be understood that each point source projects a separate cone beam. The central axis of each cone beam intersects the other cone beam central axes at a central point 15 in the middle of the tube or in the middle of the cell within the tube, as the case may be. Each time the tube is rotated by a desired incremental angle 16 while the arrangement of point sources and detectors remains fixed, another set of projections are collected, thus generating a new set of independent projections at different radial angles, and so on.

The computer 7 is coupled to transmit data, control signals and timing signals to the point sources 10b, sensing elements 12 and motors. The computer may comprise a known computer or plurality of computers and array processors adequate for image acquisition and image reconstruction processing.

The reconstruction cylinder in this new configuration, can be designed more optimally as compared to the FOT design. In particular, because the object of interest can be rotated, a reconstruction cylinder may advantageously be designed with a single point source and detector pair that creates and captures the projection image (sometimes known as a shadowgram) at each rotation angle.

In the example embodiment shown in FIG. 2, one example VOT configuration has nine fiber optic point sources arranged at twenty radial degrees spacing around a circumference at the tube wall. The opposing nine detector surfaces are arranged on a wider circumference in the same plane as the point sources. Each point source projects a cone beam onto a detector area such that the projected cones do not overlap on the detector. The central axis of each cone beam intersects the other cone beam central axes at a central point in the middle of the tube or in the middle of the cell within the tube. Each time the tube is rotated by a 2 degree increment another set of projections is collected, so that after 10 incremental rotations, a total of 90 independent projections have been generated at each 2 degree increment around 180 radial degrees of circumference. Similarly, if the tube containing the object of interest were centered and rotated through twenty 1 radial degree increments, then 180 unique projection images would be created. After a suitable number of projections have been created, the cell of interest or tube containing other cells of interest may be translated in the z-direction to accommodate a new view and repeat the image collection process.

In this design, a semicircle of equally spaced point sources have opposing detector arrays positioned around an opposite semicircle, and all elements of the imaging system are positioned on the same central plane generally perpendicular to the tube axis. However, the point source/detector combinations need not lie on the same central plane, and point sources may be spaced at unequal intervals and advantageously be interspersed between detector arrays.

As also shown in FIG. 2, because of the unbounded nature of the tube in the z-direction above and below the circle of point sources and detectors that comprise a reconstruction zone 51, it may be useful to position additional sources 10a, 10c and additional detectors 50a, 50c above and below the reconstruction zone 51 to generate images for improving the accuracy of the computed image reconstruction. Note that in a particular embodiment, the reconstruction zone may comprise a plane defined by the placement of a set of point sources and detectors. These configurations would apply to the flow optical tomographic (FOT) system design as well.

Figure 3:
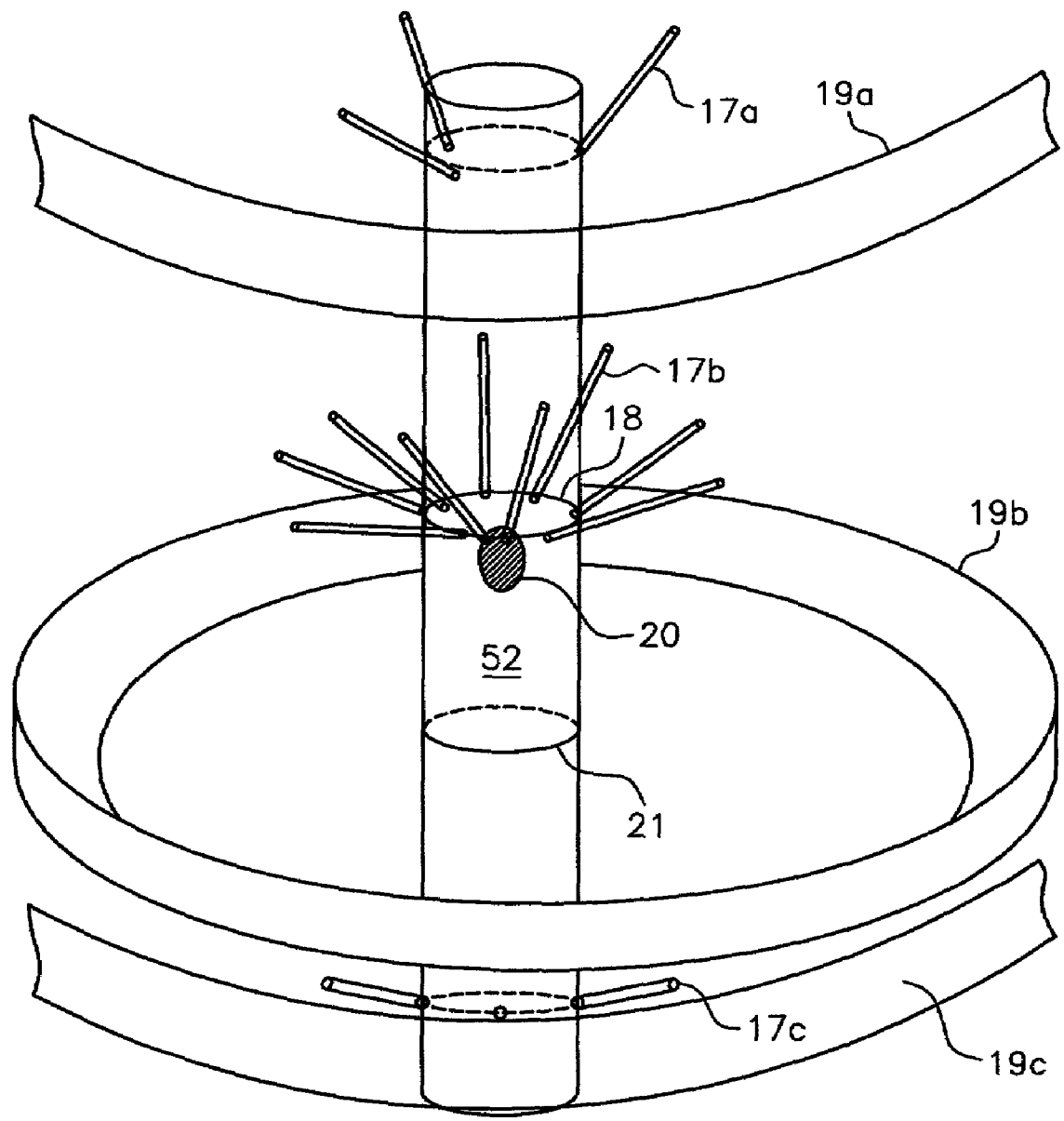
FIG. 3 schematically shows an example of an alternate system for variable-motion optical tomography (VOT) as contemplated by an embodiment of the present invention.

Referring now to FIG. 3, there shown is an example of an alternate system for variable-motion optical tomography (VOT) as contemplated by an embodiment of the present invention. A particularly useful design includes placing a ring of point sources 17b in a plane 18 located just above or below proximate a ring of detectors 19b located around a detector plane 21 such that the projection cones are aimed at their respective detector surfaces and the center of the cell 20 is located between the two planes at the point where all projection cones overlap. In this configuration, the cell can be sampled around a full 360 degree radial circumference to achieve an optimal image reconstruction, given an adequate number of point source/detector pairs, and as such, rotation of the tube is not required. Again, it may be useful to position additional sets of optical point sources 17a, 17c and opposing detectors 19a, and 19c above and/or below a reconstruction zone 52 to improve the accuracy of the computed image reconstruction. In the example of FIG. 3, the reconstruction zone 52 is located above and/or below plane 18. This geometry also applies to the FOT.

In the preceding example, 3D image reconstruction is accomplished using 2D projection images from cone beam geometry. It is also possible to use fan beam geometry whereby the 3D image is generated by stacking contiguous planar images reconstructed from linear (1D) projections using fan beam reconstruction algorithms. With fan beam geometry, the plurality of optical point sources 10b that are collimated to emit fan-beams, in conjunction with opposing detectors 12 mounted around a circumference of the tube can sample multiple projection angles through the entire cell 1 as it is moved past the sources. A cell is thus optically sectioned with projections through the cell that can be reconstructed to form a 2D slice in the x-y plane. By stacking or mathematically combining sequential slices, a 3D picture of the cell will emerge. The 3D picture of the cell can yield quantitative measures of sub-cellular structures and the location and amount of tagged molecular probes that provide diagnostic information.

Light Source.

Each source may have the same general characteristics, preferably:

- it may approximate a small circular point source for use in cone beam geometry,
- it may be bright, uniform and with known spectral content,
- the photons emitted from the source may have a known geometry such as a cone beam or a fan beam.

Further, the wavelength of the sources is selectable either by use of various diode emitters or other lasers or by bandpass filtering of a white or other broadband source, for example a mercury or xenon arc lamp.

There are several options that can be employed to create optical point sources, such as:

- a pinhole in front of a laser or other high intensity photon source,
- an optical fiber with a small cross-section and small apparent aperture,
- a short focal length lens in front of a photon source,
- an electron beam that irradiates a point on a phosphor surface (a form of CRT), and
- various combinations of the above.

The geometry is such that, the closer the point source to the object of interest (the cell), the higher the magnification due to the wider geometric angle that is subtended by an object closer to the source. Magnification in a simple projection system is approximately $M=(A+B)/A$, where A is the distance between the point source and the object (cell) and B is the distance between the object and the detector. Conversely, if the required resolution is known in advance of the system design, then the geometry can be optimized for that particular resolution. For background, those skilled in the art are directed to Blass, M., editor-in-chief, *Handbook of Optics: Fiber Optics and Nonlinear Optics*, $2^{nd}$ ed., Vol. IV, Mcgraw-Hill, 2001.

Figure 4:
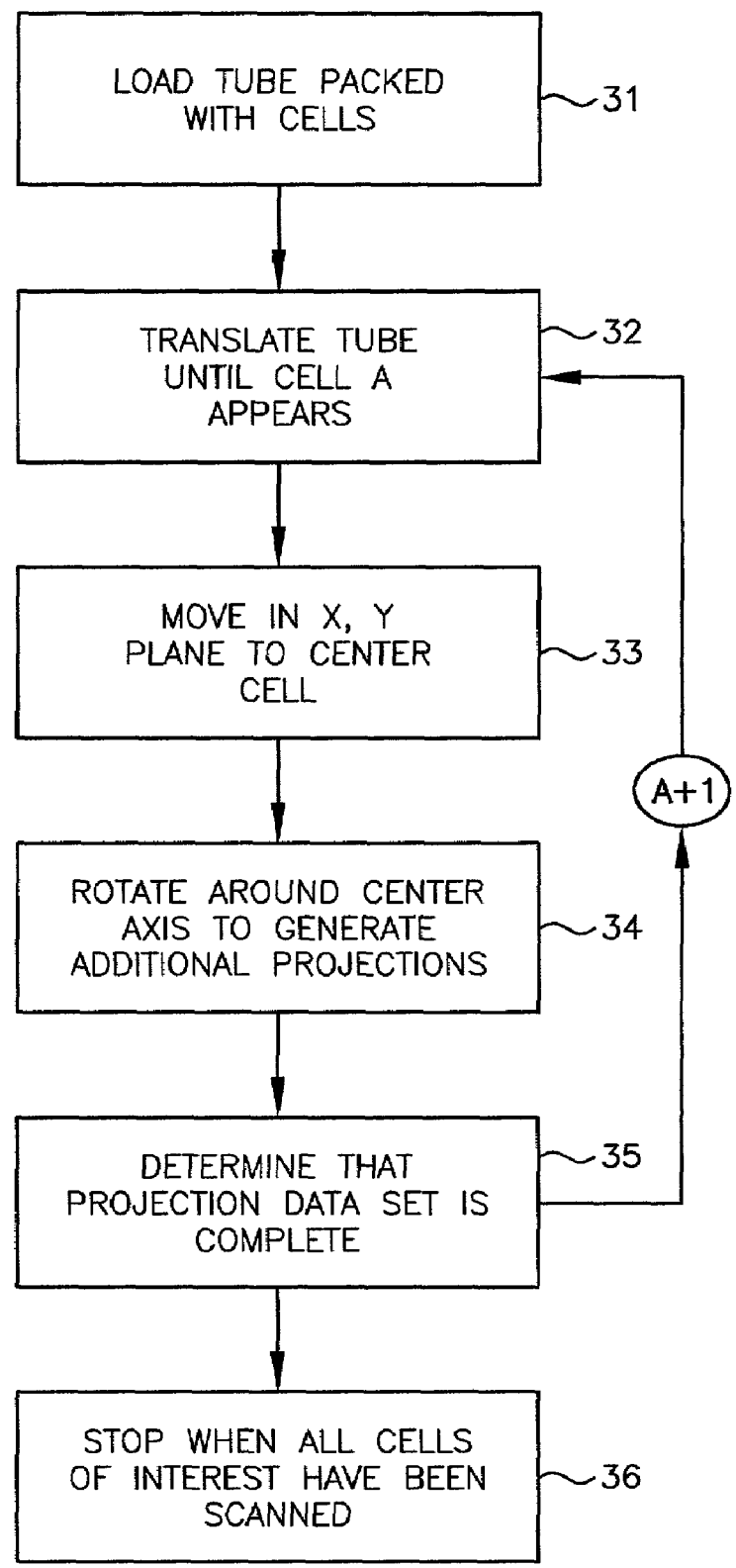
FIG. 4 schematically shows an example of a flow diagram illustrating three-dimensional (3D) image reconstruction as contemplated by an embodiment of the present invention.

Referring now to FIG. 4, an example of a flow diagram illustrating three-dimensional (3D) image reconstruction as contemplated by an embodiment of the present invention is shown. As contemplated by one example of the present invention, a 3D image reconstruction process 30 includes the steps of loading the tube packed with cells at step 31, translating the tube until the first cell of interest has been located at step 32, centering the cell of interest, as necessary, at step 33, generating a set of projections at each different rotation angle at step 34, determining when the data set is complete at step 35, and repeating the process from steps 32 through 35 until all cells of interest have been analyzed. The process stops at step 36. The process may be implemented in a computer software program executed by a personal computer such as computer 7, for example.

Image Reconstruction.

The most common and easily implemented reconstruction algorithms, known as filtered backprojection methods, are derived from a similar paradigm in computerized x-ray tomography (CT) using cone-beam and fan-beam geometry. (See the following references, for example, Kak, A. C. and Slaney, M., *Principles of Computerized Tomographic Imaging*, IEEE Press, New York, 1988, and Herman, G, *Image Reconstruction from Projections: The Fundamentals of Computerized Tomography*, Academic Press, New York, 1980.) These methods are based on theorems for Radon transforms with modifications that reflect the particular geometry of the source/detector configuration and the ray paths in the irradiating beam. However, in the case of clinical x-ray CT, the human subject is usually held motionless while the x-ray source and detector arrays may move along an arc or helix around the patient to collect data from multiple projection angles. Then the human subject may be repositioned along the z-axis and another set of data is collected, etc. Alternatively, in the more modern clinical helical CT, the patient may be continuously translated in the z-direction while the source-detector assembly rotates continuously to provide helical projection data, which is then interpolated to provide projections orthogonal to the patient z-axis.

In flow optical tomography (FOT) and variable-motion optical tomography (VOT), the object (a cell) is moved relative to the stationary sources and detector arrays wherein the plurality of source/detector systems acquire data in synchrony with specific gated time points along the cell velocity vector in a fashion that generates multiple projection angle data within a given slice or volume. For slice-by-slice scanning using a fan beam, the reconstruction algorithm will compute a 2D image of a plane perpendicular to the axis of motion, and the serial stacking of multiple slices will generate the 3D picture of the object where contrast is a function of the variations in the x-ray attenuation coefficient or optical absorption coefficient as a measure of density within the object for CT or flow optical tomography, respectively. For volumetric, cone-beam scanning the reconstruction algorithm computes a 3D image of a volume within the cell or other object directly from planar transmission or emission optical projections, where the contrast is a function of the optical density and/or tagged probe density distribution within the imaged object.

It may be desirable for either the transmission data to produce the cell density reconstruction or for the emission data (from internal sources, if any) to reconstruct the labeled probe distribution, or both, to employ image reconstruction algorithms other than filtered backprojection. The general class known as iterative reconstruction algorithms is more efficacious in some instances, especially for emission tomography or, when it is possible, as in the instance of the current invention where the axial symmetry and tricompartmental nature of the object are known, to incorporate a priori information into the reconstruction algorithm to improve the quality of the reconstruction (See, for example, Gilbert, P., "Iterative Methods for the Three-dimensional Reconstruction of an Object from Projections," Journal of Theoretical Biology 36:105–17, 1972, and other references noted hereinabove).

Figure 5:
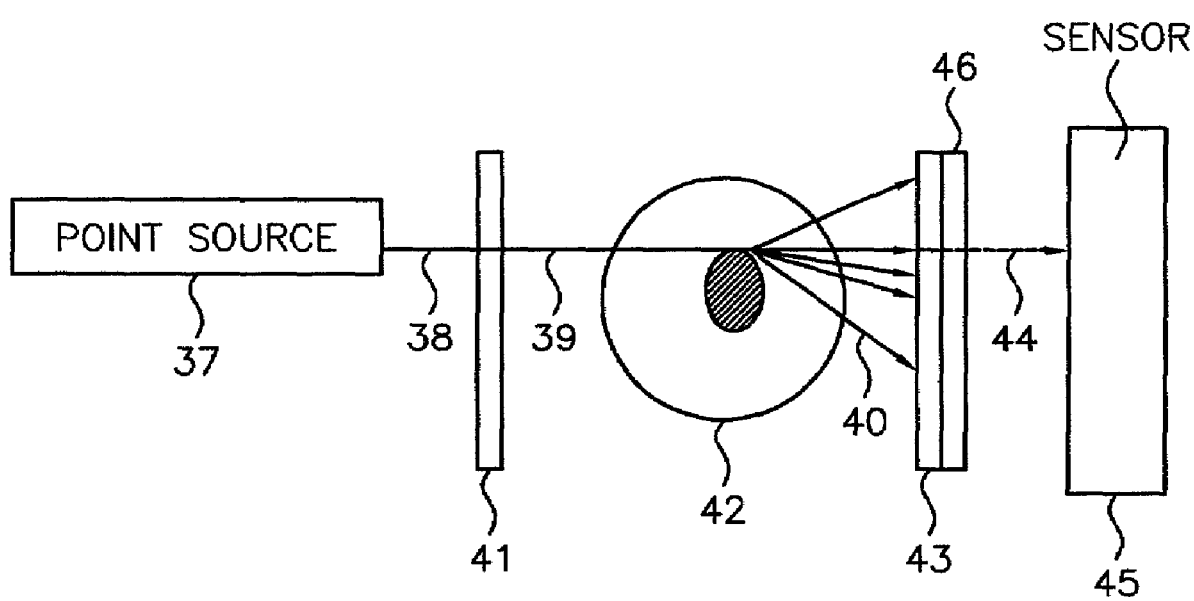
FIG. 5 schematically shows an example illustrating the use of polarization filters and/or phase plates in a three-dimensional (3D) image reconstruction as contemplated by an embodiment of the present invention.

Referring now to FIG. 5, there shown schematically is an example illustrating the use of polarization filters (and/or a phase plate) in a three-dimensional (3D) image reconstruction as contemplated by an embodiment of the present invention. All image reconstruction algorithms are vulnerable to various forms of noise in the projection data, such as scatter and diffraction. Light scatter and diffraction may become significant in optical tomography where the wavelength of the illuminating photons is of the same order as the desired resolution within the object to be reconstructed and where the object contains structures that are of the same order in size as the illuminating wavelength. Interactions that can change the polarization of photons or cause a phase shift provide an opportunity to remove or reduce the contamination in a projection image through the use of polarization filters and/or a phase plate. For example, if a point source 37 is filtered through a first linear polarizer 41, then a first polarized light ray 39 is produced that impinges on object 42. Rays 40 represent photons scattered as a result of the first polarized light ray 39 impinging on the object 42. A surface of a sensor 45, positioned to sense a projection image generated by the point source 37, is similarly filtered through a second linear polarizer 43 having the same orientation as the first linear polarizer 41. As indicated by the rays 40, photons whose polarization vector has shifted will be removed from detection. At the same time, unscattered light rays will pass through both polarization filters resulting in a portion of unscattered light 44, impinging on the sensor 45. To remove phase shift, a phase plate 46 can be placed proximate the second linear polarizer 43. In this way, the background of noise due to shifts in polarization and phase can be reduced significantly.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices and reconstruction algorithms, and that various modifications, both as to the equipment details and operating procedures, may be accomplished without departing from the true spirit and scope of the present invention.

What is claimed is:

1. A method for variable-motion optical tomography of an object of interest, comprising the steps of:
    (a) packing a plurality of objects of interest into a tubular container so that the plurality of objects of interest remain stationary within the tubular container, the tubular container having a central axis;
    (b) illuminating the plurality of objects of interest with at least one optical projection beam;
    (c) translating the tubular container until at least one object of interest is located within a region of the at least one optical projection beam;
    (d) centering the at least one object of interest as necessary;
    (e) rotating the tubular container holding the at least one object of interest through a plurality of radial angles that are perpendicular to the central axis;
    (f) generating a set of projection images onto at least one detector surface at each radial angle of the plurality of angles, where spaces between the at least one optical projection beam and the at least one object of interest and spaces between the at least one object of interest and the at least one detector surface are filled with a material whose index of refraction is matched with that of the tubular container; and
    (g) repeating the steps (b) through (f) until the plurality of objects of interest have been radially scanned.

2. The method of claim 1, wherein the at least one object of interest is a cell or a cell nucleus.

3. The method of claim 1 wherein the optical projection beam is selected from the group consisting of fan beam projections and cone beam projections.

4. A method for three dimensional (3D) reconstruction of an object of interest, the method comprising the steps of:
    (a) packing a plurality of objects of interest into a tubular container so that the plurality of objects of interest remain stationary within the tube, where an axis of rotation is aligned with a central axis of the tube;
    (b) illuminating the plurality of objects of interest with a plurality of optical projection beams;
    (c) translating the linear container until at least one object of interest is located within a region of the plurality of optical projection beams;
    (d) centering the at least one object of interest as necessary;
    (e) generating a set of projection images onto at least one detector surface at a plurality of radial angles that are perpendicular to the axis of rotation, where spaces between the plurality of optical projection beams and the at least one object of interest and spaces between the object and the at least one detector surface are filled with a material whose index of refraction is matched with that of the tabular container;
    (f) repeating the steps (b) through (e) until the objects of interest have been radially scanned; and
    (g) reconstructing a 3D image from the set of projection images.

5. A variable-motion optical tomography system comprising:
    a tubular container for holding objects of interest having a tube wall and a tube axis, wherein the objects of interest are packed in the tube so as to remain stationary relatively to the tubular container;
    a plurality of optical light sources arranged to project light round a circumference at the tube wall;
    a plurality of opposing detector surfaces arranged on a wider circumference in the same plane as the light sources, to form a reconstruction zone, so that each light source projects a beam through the tubular container onto a detector area to form projection images, such that one of the projection images does not overlap another on any of the plurality of opposing detector surfaces, and a central axis of each beam intersects the central axes of the other beams within the tube, where spaces between the plurality of optical light sources and the objects of interest and spaces between the objects of interest and the plurality of opposing detector surfaces are filled with a material whose index of refraction is matched with that of the tube; and
    means, coupled to the tube, for rotating and translating tubular container in a variable motion.

6. The system of claim 5 wherein the means for moving comprises a computer controlled motion apparatus.

7. The system of claim 5 wherein the means for moving comprises a means for rotating the tubular container such that a set of projections is collected each time the tube is rotated by a rotation displacement value.

8. The system of claim 5 wherein the plurality of optical light sources comprises two or more point sources.

9. The system of claim 5 wherein the plurality of optical light sources include a semicircle of spaced point sources that have opposing detector arrays positioned around an opposite semicircle, tho spaced point sources and the opposing detector arrays being positioned on the same central plane generally perpendicular to the tube axis.

10. The system of claim 5 wherein the plurality of optical light sources and the plurality of opposing detector surfaces lie in the same plane, and the plurality of optical light sources are interspersed between detector arrays.

11. The system of claim 5 wherein additional sets of optical light sources and detectors are positioned above and/or below the reconstruction zone to provide additional projection data.

12. The system of claim 5 wherein at least two polarization filters are positioned between the plurality of light sources and the plurality of opposing detector surfaces.

13. The system of claim 5 wherein at least one phase plate is positioned between the object and the plurality of opposing detector surfaces.

* * * * *